United States Patent
Weiss et al.

(10) Patent No.: US 6,825,329 B2
(45) Date of Patent: Nov. 30, 2004

(54) HUMAN PEM AS A TARGET FOR BIRTH CONTROL AND TREATMENT OF ALZHEIMER'S DISEASE

(75) Inventors: Bertram Weiss, Berlin (DE); Christoph Geserick, Berlin (DE); Bernard Haendler, Berlin (DE)

(73) Assignee: Schering Aktiengesellschaft, Berlin (DE)

( * ) Notice: Subject to any disclaimer, the term of this patent is extended or adjusted under 35 U.S.C. 154(b) by 282 days.

(21) Appl. No.: 09/867,753

(22) Filed: May 31, 2001

(65) Prior Publication Data

US 2002/0048764 A1 Apr. 25, 2002

(30) Foreign Application Priority Data

May 31, 2000 (DE) .......................................... 100 27 170

(51) Int. Cl.⁷ .............................................. C07H 21/02
(52) U.S. Cl. .................................................. 536/23.1
(58) Field of Search .......................... 530/350; 514/12; 536/23.1; 435/2, 6, 368

(56) References Cited

U.S. PATENT DOCUMENTS

2002/0132753 A1 * 9/2002 Rosen et al. .................... 514/1

OTHER PUBLICATIONS

Tim Reid et al., Identification and Characterization of hPEM–2, a Guanine Nucleotide Excahange Factor Specific for Cdc42, Nov. 19, 1999, Journal of Biological Chemistry, vol. 274, No 47. pp33587–33593.*

The Pem, Homeobox Gene, Androgen–Dependent And Independent Promoters And Tissue–Specific Alternative RNA Splicing, Mar. 22, 1996, Sourindra Maiti et al.

Androgen regulation of the Pem Homeodomain gene in mice and rat Sertoli and epididymal cells, The University of Texas M.D. Anderson Cancer Center, Sutton KA et al.

XP–002258615—Dec. 21, 1999, Leonard, S. et al.

XP–002258616—Dec. 16, 1999, NCI–CGAP.

XP–002258624—Maiti Sourindra et al.: "The Pem homeobox gene: Rapid evolution of the homeodomain, X chromosomal localization, and expression in reproductive tissue".

XP–002258614—Geserick Christoph et al.: "OTEX, an androgen–regulated human member of the *paired*–like class of homeobox genes".

Chad M. Wayne et al.—"Two novel human X–linked homeobox genes, hPEPP1 and hPEPP2, selectively expressed in the testis".

* cited by examiner

*Primary Examiner*—Robert A. Wax
*Assistant Examiner*—Robert B Mondesi
(74) *Attorney, Agent, or Firm*—Millen, White, Zelano & Branigan, P.C.

(57) ABSTRACT

The invention relates to the human PEM polypeptide that plays an important role for the maturation of sperm and for Alzheimer's disease, and the nucleic acid that codes for them. The invention comprises the use of PEM as a target in male birth control and for the treatment and diagnosis of male infertility and Alzheimer's disease. The invention also includes a selection process for PEM antagonists as well as the production of binding molecules, which specifically detect PEM. In addition, genes that are regulated by the PEM gene are part of this invention.

6 Claims, 1 Drawing Sheet

A.

B.

SEQUENCE LISTING

<160> NUMBER OF SEQ ID NOS: 6

<210> SEQ ID NO 1
<211> LENGTH: 577
<212> TYPE: DNA
<213> ORGANISM: Homo sapiens

<400> SEQUENCE: 1

```
tccaacatca ggcgctccag ccatggcgcg ttcgctcgtc cacgacaccg tgttctactg      60
cctgagtgta taccaggtaa aaataagccc cacacctcag ctgggggcag catcaagcgc     120
agaaggccat gttggccaag gagctccagg cctcatgggt aatatgaacc ctgagggcgg     180
tgtgaaccac gagaacggca tgaaccgcga tggcggcatg atccccgagg gcggcggtgg     240
aaaccaggag cctcggcagc agccgcagcc cccgccggag gagccggccc aggcggccat     300
ggagggtccg cagcccgaga acatgcagcc acgaactcgg cgcacgaagt tcacgctgtt     360
gcaggtggag gagctggaaa gtgttttccg acacactcaa taccctgatg tgcccacaag     420
aagggaactt gccgaaaact taggtgtgac tgaagacaaa gtgcgggttt ggtttaagaa     480
taaaagggcc agatgtaggc gacatcagag agaattaatg ctcgccaatg aactacgtgc     540
tgacccagac gactgtgtct acatcgtcgt ggactag                              577
```

<210> SEQ ID NO 2
<211> LENGTH: 184
<212> TYPE: PRT
<213> ORGANISM: Homo sapiens

<400> SEQUENCE: 2

```
Met Ala Arg Ser Leu Val His Asp Thr Val Phe Tyr Cys Leu Ser Val
 1               5                  10                  15

Tyr Gln Val Lys Ile Ser Pro Thr Pro Gln Leu Gly Ala Ala Ser Ser
                20                  25                  30

Ala Glu Gly His Val Gly Gln Gly Ala Pro Gly Leu Met Gly Asn Met
            35                  40                  45

Asn Pro Glu Gly Gly Val Asn His Glu Asn Gly Met Asn Arg Asp Gly
    50                  55                  60

Gly Met Ile Pro Glu Gly Gly Gly Asn Gln Glu Pro Arg Gln Gln
65                  70                  75                  80

Pro Gln Pro Pro Pro Glu Glu Pro Ala Gln Ala Ala Met Glu Gly Pro
                85                  90                  95

Gln Pro Glu Asn Met Gln Pro Arg Thr Arg Arg Thr Lys Phe Thr Leu
                100                 105                 110

Leu Gln Val Glu Glu Leu Glu Ser Val Phe Arg His Thr Gln Tyr Pro
            115                 120                 125

Asp Val Pro Thr Arg Arg Glu Leu Ala Glu Asn Leu Gly Val Thr Glu
    130                 135                 140

Asp Lys Val Arg Val Trp Phe Lys Asn Lys Arg Ala Arg Cys Arg Arg
145                 150                 155                 160

His Gln Arg Glu Leu Met Leu Ala Asn Glu Leu Arg Ala Asp Pro Asp
                165                 170                 175

Asp Cys Val Tyr Ile Val Val Asp
                180

<210> SEQ ID NO 3
<211> LENGTH: 10968
<212> TYPE: DNA
<213> ORGANISM: Homo sapiens

<400> SEQUENCE: 3
caatacaaga gaatgtctgt gttaagataa ggggttgtgg agaccaaggt tcccattatg      60
cagaggaagc ctccaggtag ctggcttcag agagaataga ttgtaaatgt ttcttacttg     120
agttgattct ctcctggatc aagaaaaagg cctgcacaag aaagggggatt ctcttgagaa    180 tgtacatttc cccccacaag agacagcttt gcaggactgt ttcaaaatat gacaaagaaa     240 cacataggggt aaaatacttt tgatttcttt caagccttgc tatctgtcat gtgatgctat    300
actagagtta ggctggaaat tggtgtctta ttgccacaga gtatgttagt cttaagttct    360
gttctaacgt taagactggt cagctgtaca cgaattccaa aagggagtag ggaataataa     420
ggcatgtctg acgcctactt cctgtcatga cctgaataag ttttcaggt taactttgga     480 atgcccttgg ctgagaggag ggatccattc agatagttgt ggggcttcga atttatttt    540 tggtttacaa tagcatgaac aaagcagagg tctgacagct tcgttccagt gagtggatat     600
tctggaacat tgctcagggt accatcttct tactcttctt tgagcagcac taaatgaaaa     660
ggtccccttt caccttgtaa tcagcaggaa gtgggattct ctcgaagatg ttgaagatga    720
caaaataaac ttaaaggatt gttcatctgc ttttgagcta gggaaggtat aacaatatgc     780
tttctgggcc gggggggaggg gagaaaatgg agaagagcct cttttttggc ttaatgaaat    840
ttttgcttgt gtttctttg aagcagcagg atctttgggg cagaatagct cctattcccc    900
tgtgtccccc acaaaaaggg agggcagtga acagaatttg gagcatagtg gagtggatca    960
acgttcagct gccaccttcc cataaatcct atgagtagcc acctaggaag tttctcttta   1020
```

-continued

```
gagtccagaa tttggactga actagtcagc ataactggaa ctcagcttta tctgggaata   1080
cactgttgtc tcaccaggaa tctgcttcac cccttcttgc acatatttgt ggtccctaaa   1140
ggggcaaggt ggtgaggatg gcataatggc aggggtaggg aggggagtg gagaaggatg    1200
tatgggtcag tgcaaactca caatgacgct tggtaaactt ctgtgatgtg cagggcctat   1260
tgttgatggc aagccaggga tgtcatttca tgaaagatct ccttgtcatt ttgtttaaat   1320
ggctttcttt ttttttttt ttgatatgga gtctcactct gttgcccagg ctgaagtgca    1380
gtggtgcgat cttggctcac tgcaacctct gcctcctggg ttcaggcctc ccgcatagct   1440
gggattactg gtgcctgcca ccacatccag ctaatttttt tgtattttg atagagacag    1500
ggtttcacca tcttggctag gctggtcttg aactcctgac ctcctgatcc acccgcctca   1560
gcctcctaaa gtgttaagat tacaggtgtg agccactgca cctggcctta aatggctttt   1620
taaaaacaat ttgcacctat accctactaa ccacaattgg cacacaaaaa caaatatatt   1680
gagaatttgc ctctttattg ataacataag tgcagaggga ataaggggtag cctgagcggc   1740
atgggcagcc caggtgtcag tggcaccaga aaaacccatc tccaaactag ctcctgaaga   1800
aggatggcat tctagggcta gtccacgacg atgtagacac agtcgtctgg gtcagcacgt   1860
agttcattgg cgagcattaa ttctctctga tgtcgcctac atctggccct tttattctta   1920
aaccaaacct acaatcagag ggaaaagggg attggtttag tatattgaac agttaatgtc   1980
gtaatagaaa aacacaggat gcaactttat atgctattga gattttaaac tgcatcagga   2040
aaagctattt cctcattgct aaaatacctt aggaaagtta acaacatagc ccgtggccct   2100
tcagctcacc cttagtgagg accagctttg tgccaagtcc tggaataagc ttattacttt   2160
gtatctctct tctccatttt atttatttat ttatttatta tttatttatt tatttattta   2220
tttattttt gagacagggt cttgctgttt tgcctgggct gggatccagt ggtgcaatca    2280
tagctcactg tgacattgaa cttctgggct caagagatcc tcccacctca ccctcccaag   2340
tagctggtac tagaggtaca tgccactatg cccagctgtt ttaattttc tgtagagaca    2400
gggtctcgct atgttgccca ggctggactt gagctcctgg cctcaagtga tcttcccacc   2460
ttggtgtccc aaagtgttgg gattacaagc gtgagccact gtgcccagcc ccaatttaa    2520
tattcttaa tggttacttc cagatattgg atgcagttct ggcttatgag ttgttccagg    2580
tccttgctgt ttgttaattc aatgcctggc aacagggtaa caaaaggtgt gcatctgaca   2640
agtgaccatc aactatccag ctgcctcctg ctccctcctc actagggaga gtttcatctt   2700
gtttgtggga gaagttcggc atggtaaaaa gtgggcctaa tttcaaatca ttttcagggg   2760
attgtttaaa aaatccatct ttagtatgta gtaaataata ggaaagagcg cactggaatt   2820
ttagacaggt ttccttccag gatgtctaag ggatcattcg tcctctggca agagaggcct   2880
ggacactgcc ttgatatttt agcctgtagc attaaggaaa gttgaaacca gctcgaccca   2940
aattaactga aactctcaaa atctttgct cacccaatag tttaggggaa agaggcatac    3000
cattgtcacc aatgccaaat cttcgttctc caatctgctg cactctccaa accttcctgg   3060
gctcaggaca aggtcagctc actctgtttt acctacagct ccaggatcct ggactggagg   3120
tgctgtagcc cagtaaggca gggcccccta ggccctgcta ctcaaccagg agatctgaat   3180
cccacccct attcctaagg cagaaaggtg gaaccagcat tttaggaaga tggttaacat    3240
caatgtgggg gaagggtcac aaatatggct cctccctaaa tatctgccaa caattaaaaa   3300
gcaaacagac aaaaaaagcc tgtcagttag atgtcactat cctctcagca acctagttaa   3360
cggagtttat attgtatttta ttactttcaa aagttctcaa actgcaaatt gtaagctgca  3420
```

-continued

```
caaagggcct tctttctcta cctgacacgt cttttttcact ttcccagtta aggatttgca    3480
gtatttctgc tgcatgaggc cagtctctaa aagtctaaaa gagctcattt tgggagcttt    3540
caagtgtacc actggtcaaa tctctataaa cataaccaaa gtgtacagtg ggttaactgg    3600
tatgttctga tactaggtct gcattcccaa tactggtttc ataaaccagt tgcattacat    3660
ctgcaaaagc tatggggaaa ctatgtatta cttttcttggg ggaaatttat gctgtatagt    3720
ttggagatac atgagagcat tctgtctctt cccttatttg tatcttgtgg ctcatattct    3780
tttcagagca ctaaggagag aacattatgt cgactcaggg aggagaaaaa caactcacca    3840
agccttgttt ttcttttcct ctgagtttgc cttaccagct ggagaaaagt gatcccaacc    3900
tcttttcaac ttctccaacc cgaaccaggt gtgattgtga gtccacccct tgccattagg    3960
atgccagcac tcagtaaccc gctttgttag tttgcttttt tggacaaccc actaccagat    4020
cggcagtgca tttccctcac tacactcaca catgcactct gcataaaagc taataataag    4080
gtcatcctga ttttttgtttt tctttttttg ggaaaacatc actttgatac tatgtatggt    4140
tttctttggt cttaagtggt catcacttga atcctatgac ctactaatta gttaacactg    4200
cttaaaggaa tgaaaagtat ttgaaattaa catgggtgtg aatctaccct aaaatgaggg    4260
ccacctctcc aaacaaattc cagaaaaccc acctcttcaa aaaagtacca ccaaaaagaa    4320
atataaatcc ttagatggat agaaattcct caagagaaca gtcacttaaa catttagtag    4380
tttcataatg ttgaatttgt atagtacatg catagtatgt gcaaagccta ttttgaccat    4440
atttctctct aaccttttca cccttcttgg tcaactgaaa tgaattcaat attactcatt    4500
ttgtttgctt cattctttag acaattttcc aaagcataca aaccttacaa accttcctca    4560
atttcaaaat aatgtgacta ttttagcaat attttcaggt tgcacatca aagtatttta    4620 gaaaattaaa acttagggct gccactctct atactgcttt accaataact aaaaacaaa    4680 caaagaagga ccaggggctt ggacatataa gctatcttcc catcagtctc agcttaacta    4740
agtatacatt atttagtcat gtaatgtgtt ctgtgggtga attactccct catcccaata    4800
tttataaatt cactcattta gctaagtgtt tatgcctggc cttaaataat ttagtacact    4860
tgaaccctct tataaccctg ctcctccctg cattaacttg aatacttcta aggtaagact    4920
gaaccccacc atgactctac acagaaattg ttcctaaaag ataccagcgt tagaaggagt    4980
tgaattttat ttattggata catacatata tgtataatat ataatacaca tatgtgtatt    5040
atacattatc atacatatat gtattatata ttacacatat atgtataata tataatacac    5100
atatgtatta tataataatac atatatgtat aatatatgtg tttcatatgt atgtatttgt    5160
ttaattttgt atacagatta ggagaagcag ttttttgtttt gttttttcctt taggaaatca    5220 tattccctaa ttggaatggg aaagaggaaa gaaccataag ctggagctta cttccttttc    5280
taccgacaag gaacccaaac ttcaaaactt atttgtcaac ataaaaaaga caataataaa    5340
aacaacaact ttagaacgtt caggacaaag ccttcaaagc cttcaatgcc ctgaagcagg    5400
ttttagaatg gctgtcctct caaattgctt tttcaagtgt actgacccgc actttgtctt    5460
cagtcacacc taagttttcg gcaagttccc ttctgtggag agaagatcac acatggttag    5520
tattcaaagt tgtggatgaa atgaaatata tagtatgtac tatttacttc atgcttgttt    5580
tacaatttat aatctcccct cacacctccc ccaagtatat acttttctct aattcccagc    5640
tccatggttg ctttagaaat ggtttaccct catcacgaaa tttaaggtga cgttaacaac    5700
tcagtaatca agagaaatac cttttttttt ttaaattgag acaaggtctc actctgtctc    5760
```

-continued

```
ctaggctgga gtgcagtggt gtgatttcag ctcactgcaa cctccgcctc cggggttcag      5820
acgattctcg tgcctcagcc tcccgagtag ctgcgattac aggcacatac caccatgccc      5880
agttgatttt tgtattttta gtagagatgg ggttttgcca tgttggccag gctggtctcg      5940
aactcctgcc cgtctcagcc tcccaaagtg ctgggatttg gggcatgaac caccgcaccc      6000
ggccaagatg aataatttaa tgcattatta ttatttttat tattattatt tgagacaggg      6060
tctcactgtc gtctatgttg gagtgcagtg gcaggatcac tgctcactgc agcctgcatg      6120
tcctgggctc gaacgatcct cctgcctcag ccttccaagt ggctgggagt acaggcacac      6180
accaccacac ccacatggct aattttttaa gttttattta gagacggggt tttgccatgt      6240
tgcccaggct gttcttgaac tcctggactc aagcaacctt cccaccttgg cctcccaaaa      6300
gcgctggaat tacaggcctg agccaccgtg cctggcccta atgcactatt ttaataaata      6360
acaattaatg caaaaatctg tgatgaggac caggcactgt ggctcaggcc tgtaatccca      6420
gcagtttggg aggccgaggc aggcaaattg cttgagccca ggagtttgag actagcctgg      6480
gcaacacggc gaaaccttat ctctacacac aaaaaaaata caaaaattag ccaggtgtgg      6540
tggcctgtgc ctgcagtccc agctactcag ggggctgaca cgggaggatg gcttgaaccc      6600
aggaagcaaa tgttgcagag agctgaaatc gcactgctgc actccaacct gggccacaga      6660
gagagactct gtctcaagac aaaacaaaaa accagaaaa acaaaaaacc aaccaaacaa       6720
acaaaaaaaa actatgatga caaattatc aaaattttaa ataaggaag gatctagcac        6780 tgtagttgca tgacagtacc tcattctcct tacccaatt tcaataaaat tttatttata       6840
aaaacagacc acagctgggt gtggtggctc actcctataa tcccagcaac tcaggaggct      6900
gagatgggag gattgcttgg gtgacagatc ccccactcaa caaaaacaac aacaacaaca      6960
aaaacaggcc atcatcacag gtaataaaag aaaaaataca taacttggac tatatcaaaa      7020
tttaaaactt ctgtatatca aaagatgcaa tgaacagagt aaaaagacaa ctcatagaat      7080
ggaaggaaat atttgcaaat cacatctgat aagggggttaa tatccagagt gtataaagaa     7140 ctcctcacaac ccaataacca aaaaaaaaga aagaaagaaa gaaaaagcca ctcagatttt     7200
aaaatgggta aaggacttaa agagatattt ctccaaagaa gatatacaag tggccactaa      7260
gcacatgaaa ggatgcacaa catcactaat cattagggaa aagcaaatcg aaactacaat      7320
gaagtatcac ctcacacccca ttaggatggc tatgtaaaaa accccagaaa ataacaagtg     7380
ttggtgagga tgtggagaaa ctggaaccccc catgtactgt tggtgtgcac ctgtatctat     7440
aaaatggaat attatttagc cttaaaaagg aaggaaattc taatatatgc tgcgatatgg      7500
atgaaccttg aagaccttat gctaagtgaa ataagtcagt gacaaaaatg caaatactgt      7560
atgattctac ttacatgaga tacctagagt agtcaaaatc atagagacat aaaatagtag      7620
aatggtggtt gccaagggct ggggaaaggg ggaaaagggg agttgcttaa ctggtataga      7680
gacttagctt ggcaagatga gaagaattct agagatctat tgcacaacaa tgtgaacata      7740
cttaacacaa ctgaactcta tacttaaaaa gtggtttgga cggtaaattt catatttccg      7800
tgtattttac cacatctttta taaaagggag gcacggacta gtttccaggt ttcattcaca     7860
taaacattgc aataaaacat ttaccttgat gcccaggagg taaatatccc cctccacacc      7920
agcacaaagg caggcaagga cccccagtgg cttttttcctc atgattgggt ggggcaaggg    7980
agagaaaaag atgcctcgaa acgaacttgg agatctcgtg gctcctggag caggccactt      8040
accttgtggg cacatcaggg tattgagtgt gtcggaaaac actttccagc tcctccacct      8100
gcaacagcgt gaacttcgtg cgccgagttc gtggctgcat gttctcgggc tgcggaccct      8160
```

-continued

```
ccatggccgc ctgggccggc tcctccggcg ggggctgcgg ctgctgccga ggctcctggt   8220
ttccaccgcc gccctcgggg atcatgccgc catcgcggtt catgccgttc tcgtggttca   8280
caccgccctc agggttcata ttacccatga ggcctggagc tccttggcca acatggcctt   8340
ctgcgcttga tgctgccccc agctgaggtg tggggcttat ttttacctgg tatacactca   8400
ggcagtagaa cacggtgtcg tggacgagcg aacgcgccat ggctggagcg ctgcgcccct   8460
gcacaaactc cgtggcgtct gcagctggag tggggttag agggtggagc tagttcctgt    8520
tctcatgctt ggtattggtt acagttgcaa tgagtgggac ttgcttatgc gcacaagcaa   8580
gagagggaat ggagaggagt gggggatgg gaagttgggg ggtgcgggtg gggagtgggg    8640
gtgttgcagg tgggagtggg gggttgtgag tgtggggtgg ggtgcaggtg gggatggggg   8700
tgtgggtgga gggtgggggg tgcacagtga gggtgggggt tgcgggtgag ggtagggggtt  8760
gtgggttggg gtggggggttg ccggtggggg tacatggtgg gggtgggggt agcgggtgga  8820
gatgggaggt gtgggtggag ggtgcgtggt gggggtaggg gttgtgggtg ggggtgaggg   8880
gtgtggtatg ggtcgtgggt gggggtggca gttgaggggtg gagtgggggtg gccaaaacac  8940
aggggcagtg tggagaagaa aagggccaat aggaggcata tatgtatgca acatggggcc   9000
ccagcttgca gctttgctga ctacacccta ctcgggccta gttattaccc tgaggaaagc   9060
tgatttgggg gctcagaggg gaggtgagat ctcacggtga ccataggacg ccttgagtaa   9120
aagtttggag aatatctcat ggcctgaccc tccatatttg gcagcatgca cagggcgcgg   9180
gctattaatt aagcagaaat gattgactgg gggctgcttg ttcagagttc cagcaaaggc   9240
actgaaagca gagctgccat gctctcttca gtgctgggat cgggatcttg gagatgggca   9300
tgcagagcat tctgggtggt aagatgtgct ctgcaagaaa tctaacgcac cctttgagaa   9360
agtcaacaca gaataaacac gaggctgaat ctgttagcct gagactgaat atctttggct   9420
atgcaagaga aacctgtact catggcaaaa tggagtgcta taaggacaag caaaaaataa   9480
ataaataaat aaaatcgggg atggtatagg aagagcacca gtaagggcat acctgccaaa   9540
aatctccaat cttgggatgg agatttggga tttatggata tgcagcttac tggatgtggg   9600
gccacttctg ctccacagag ccttgtaact acacagcctt cctaccactg accccaataa   9660
gcccaattac gaagaaaaac cctgaagagc ctggtcagt ggctcctgca ctagtcccag    9720
ctactcagga ggctgagatg ggaggatcac ttgaacccag gagtttgagg ctgtggtgag   9780
ctagaatcac atggcagcac tccagcctgg gcaacagaca gaggcccctt tctttaaaa    9840
taaataataa aataagaaat aaaatgaaaa tgaaagaaag gaaagcgcta agagagtctg   9900
tcatgaggaa gggcatggag atgtcttttg agggtggaca actcatgaat ccttaatttt   9960
tctagagatt gtgtgtgtgc tcttaagtga tgttatatac tttattttgt tttttaaaaa  10020
tatttttaaa aattttattt ttaaatgttc ttttaaaaac tttctgtatc tatttatatc  10080
tattggttat ttgaggattt tttggcagca tatataaata tgcagaccct ttgagtctgt  10140
agcctaccaa gagagatagc tctcgtcttc atggtgattc tgagcatgga aaggcccttg  10200
cacttggcag catgacaagg actaagccac tcgctccatt aattgactgc catccactgg  10260
gctaagtgag atccttgcgt tctatcccta gtgagagaag agagaggaag aagaagaaaa  10320
atagaaagat aataagaaaa tagaaaaaga aatgaataaa tgtacattgt ggggagcagg  10380
aaaggactac cagtaatggg aggcatcagc taggagcaca gatccgaagc atgactcact  10440
gtgtgtccta ggacactgga tgaatctatc tggttctcag cttcctcacc tataaaatgg  10500
```

```
                                                    -continued agataacaac agtgtctcga tcatagggtt ttcatgagag ttcaatgagg caaggcatac    10560
atgtaactga acacagctcc gactgctcac cagttgcaaa gtccagtgaa caagaacgac    10620
gtctggtaga aagaaagtgg ctttattcca gagctagttg aggggaagta gtacaggctg    10680
ccttgaggaa gccactaaag cctttgggc agaaggcagg agctttgaaa gtggggcttg     10740
gcgtgaatgg catgcagggg agagggcgat gaagtgcaga gtctatgtga cttgcttcgg    10800
atgtcttatc tatcaggtgg tctggctggc accgtcacgg gcagagctag gttgtaagtt    10860
gaggcaatct caatttgcct cctggtagga gagagttctg gaggttcctg gtttgcttta    10920
aggttcggtc tctgtaactt ctaagtaaac atgtagttag ataagctt                10968

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 4
atggcgcgtt cgctcgtcca cgac                                              24

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 5
tagtccacga cgatgtagac acag                                              24

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 6
ctagaagcat ttgcggtgga cgatggaggg                                        30
```

HUMAN PEM AS A TARGET FOR BIRTH CONTROL AND TREATMENT OF ALZHEIMER'S DISEASE

DESCRIPTION

The invention relates to the human PEM polypeptide, which plays an important role for the maturation of sperm and the nucleic acid that codes for them. The invention comprises the use of PEM as a target in male birth control and for the treatment and diagnosis of male infertility and Alzheimer's disease. The invention also includes a selection process for PEM antagonists as well as the production of binding molecules, which specifically detect PEM. In addition, genes that are regulated by the PEM gene are part of this invention.

The intention to use proteins of the male reproductive tract or sperm proteins as a target group for non-hormonal contraception has been known for several decades. For example, a project with the name "Vaccines for Fertility Regulation" was supported by the World Health Organization (WHO) (P. D. Griffin, Hum. Reprod., 1991, 6: 166–172). Various sperm proteins such as, e.g., PH-20, SP-10, FA-1, FA-2, CS-1, NZ-1, NZ-2 and lactatedehydrogenase C4 were proposed as candidates for immunocontraception (R. K. Naz, Immunol. Rev., 1999, 171: 193–202). Immunization tests with PH-20 showed that both male and female animals are thus completely and reversibly infertile (P. Primakoff et al., Nature, 1988, 335: 543–546). The use of the intra-acrosomal sperm protein SP-10 as an antigen caused an immunological response in women that reduces fertility (R. W. Wright et al., Biol. Reprod., 1990, 42: 693–701). Active immunization of animals with FA-1 produces a lasting and reversible inhibition of fertility (R. K. Naz and X. Zhu, Biol. Reprod., 1998, 59: 1095–1100).

PEM is a transcription factor that includes the Homeobox family. The corresponding cDNA was cloned from the mouse (M. F. Wilkinson et al., Dev. Biol., 1990, 141: 451–455) and from the rat (S. Maiti et al., J. Biol. Chem., 1996, 271: 17536–17546). PEM transcripts are expressed abundantly and selectively in the male genital tract. In the mouse, the PEM expression was mainly detected in the testes, while in the rat, PEM can mainly be found in the epididymis (K. A. Sutton et al., J. Androl., 1998, 19: 21–30). The in vivo expression of the PEM gene is regulated in these organs by androgens. In addition, PEM transcripts were described in the muscle and in macrophages, but in these cases, the PEM expression does not seem to be regulated by androgens, which can be attributed to the use of different promoters (S. Maiti et al., J. Biol. Chem., 1996, 271: 17536–17546). Despite the unremarkable phenotype of the PEM-knock-out mouse (J. L. Pitman et al., Dev. Biol., 1998, 202: 196–214), it can be assumed that the human PEM plays an essential role in spermatogenesis and/or in sperm maturation. PEM is the sole known transcription factor whose expression is regulated by androgens (S. Maiti et al., J. Biol. Chem., 1996, 271: 17536–17546).

No one has yet found the human PEM ortholog; this suggests a low sequence conservation in different organisms, as can already be determined by the weak identity (73%) between mouse PEM and rat PEM (S. Maiti et al., Genomics, 1996, 34: 304–316).

The invention relates to the identification of human PEM. Both the complete coding PEM-cDNA sequence and the structure of the PEM gene could be determined. The human PEM-amino acid sequence has only 30% identity with the sequence from the mouse and only 32% identity with the sequence from the rat. The human genomic locus could be defined in Xq 25–26.

The identified cDNA sequence is shown in SEQ ID No. 1, and the protein-coding sequence is shown in SEQ ID No. 2. The genomic sequence could also be identified and is shown in SEQ ID No. 3 (corresponding to a cross-section of nucleotides 16000–170967 from Gene Bank Accession No. AC005023). The initial exon extends from nucleotide 168 439 to 168 042. An internal exon extends from nucleotide 165 491 to 165 446, and the terminal exon extends from nucleotide 161 927 to 161 817 (111 nucleotides). In the range of nucleotides 161 698 to 161 693, there is a polyadenylating signal.

The human PEM is preferably coded by (a) the coding area of the nucleic acid sequence shown in SEQ ID No. 1, (b) one of the sequences according to (a) against the backdrop of the degeneracy of the genetic code and/or (c) one of the nucleic acid sequences that hybridize under stringent conditions with the sequences according to (a) and/or (b). The human PEM especially preferably has the amino acid sequence shown in SEQ ID No. 2 or an amino acid sequence that is at least 80%, preferably at least 90%, identical to it.

The term "stringent hybridization" according to this invention is used in this case as in Sambrook et al. (Molecular Cloning, A Laboratory Manual, Cold Spring Harbor, Laboratory Press (1989), 1.101–1.104). Accordingly, we speak of hybridization under stringent conditions, if after washing for one hour with 1×SSC and 0.1% SDS at 55° C., preferably at 62° C. and especially preferably at 68° C., especially for one hour with 0.2×SSC and 0.1% SDS at 55° C., preferably at 62° C. and especially preferably at 68° C., a positive hybridization signal is still observed. A sequence that hybridizes under such washing conditions with a nucleotide sequence that is shown in SEQ ID No. 1 or a nucleotide sequence that thus corresponds against the backdrop of the degeneration of the genetic code is detected by this invention.

In particular, this invention detects natural, allelic variations of PEM, in which these are optionally also functional mutations. Moreover, recombinant variants, for example functional partial fragments (such as, for example, the "Divergent Paired Class" homeodomains as described for the mouse of Rayle (Develop. Biol. 146 (1991), 255–257)), are also detected by this invention.

Especially preferably, the human PEM has the amino acid sequence that is shown in SEQ ID No. 2 or a sequence that is at least 80%, and especially at least 90%, identical to it. The 1% identity is in this case calculated according to the following formula:

$$I = n/L \times 100\%,$$

whereby n stands for the number of identical amino acids of the two sequences that are compared to one another and L stands for the length of the sequence section used for comparison.

The inhibition of PEM can result in the inhibition of sperm development or maturation and thus represents a novel approach for contraceptive preparations. In addition, the screening for functional mutations in the PEM gene can be used as a diagnostic agent for determining the causes of infertility. By restoring PEM function (e.g., by gene therapy), patient fertility can also be restored.

The subject of the invention is thus the use of human PEM and/or a nucleic acid that codes for this as a target substance for the production of an agent for birth control.

An inhibition of human PEM can be used for inhibiting fertility and especially for inhibiting spermatogenesis in male mammals. This is of great importance in human contraception, but also in veterinary medicine for population control. The inhibition of PEM can be carried out by expression reduction by means of antisense-nucleic acids or ribozymes or on the protein level by using inhibitors such as anti-PEM-antibodies or low-molecular antagonists. The production of antisense molecules and ribozymes can be carried out, for example, as described in Sczakiel (Antisense-Nucleic Acid Drug Dev. 7 (1997), 439–444, Lavrovsky et al. (Biochem. Mol. Med. 62 (1997), 11–22) and Thompson (Methods Enzymol. 306 (1999), 241–260). Polyclonal antibodies against human PEM can be carried out by immunization of test animals with human PEM or fragments thereof, optionally on a vehicle such as keyhole-limpet-hemocyanin and recovery of the resulting antibodies from the immunized test animal. Monoclonal antibodies can be obtained by, for example, fusion of spleen cells of the immunized test animal with myeloma cells according to the method of Köhler and Milstein or further developments thereof. Low-molecular inhibitors of PEM can be identified by a screening process as explained in more detail below.

By contrast, an activation of human PEM to increase fertility can be used. Also here, applications both in human medicine and in veterinary medicine are possible. The activation of PEM can be carried out by, for example, increasing the PEM expression in target cells, e.g., Sertoli cells in the testes and/or epithelial cells in the epididymis by means of gene-therapy methods. To this end, a nucleic acid that codes for PEM can be introduced into the target cell under the control of an active promoter in the target cell by means of suitable gene transfer vectors, e.g., viral vectors such as, for example, adenoviruses, retroviruses, adeno-associated viruses or vaccinia viruses, or plasmids, and can be expressed there. Suitable gene therapy processes are described in, e.g., Gomez-Navarro et al. (Eur. J. Cancer, 35 (1999), 867–885). In addition, an activation of PEM can be carried out by low-molecular active substances, which can be identified by a screening process as described below.

Another subject of the invention is a process for the preparation of new agents for birth control. The identification of these new agents is carried out in that the ability of test substances to modulate human PEM is determined. This determination can be performed as a high throughput test, in which a considerable number of test substances is studied in parallel. The test can be performed on a cellular basis, whereby cells can be used that are transfixed with the gene for the human PEM and are able to produce an overexpression of this gene. In contrast, cells can also be tested that contain a completely or partially defective PEM, for example cells that contain a defective human PEM gene in at least one allele, preferably in both alleles. The test cells that are used for the identification of new active substances are preferably mammal cells, especially human cells. As an alternative, a test on a molecular basis can be performed, whereby the human PEM is used in the form of cell extracts or in an essentially isolated and purified form, optionally also in the form of an active fragment.

In addition, the process according to the invention for identifying new agents for birth control can comprise the formulation of test substances that exert a modulatory action on human PEM, or compounds derived therefrom, into a pharmaceutical agent.

Still another subject of the invention is a diagnostic process, in which the expression and/or the functionality of human PEM is determined in a sample. The sample preferably originates from a patient who is to be subjected to a fertility determination or by a patient in whom the suspicion of Alzheimer's disease exists. The determination of PEM can be carried out on the nucleic-acid level, e.g., on the DNA level, for example by Southern Blot or determination of single nucleotide polymorphisms, on the transcript level by determination of the degree of expression, the expression pattern or the transcript length, or on the protein level, e.g., by immunohistochemical or immunocytochemical methods or by function measurements. The determination of single-nucleotide-polymorphisms allows the identification and diagnosis of functional mutations, which may be the cause of infertility in patients.

In addition to the role in sperm maturation, the human PEM also has a function in the case of Alzheimer's disease. Human PEM is expressed to an elevated extent in the brain of Alzheimer patients in comparison to brains of healthy humans. The inhibition of PEM can have a positive effect on the course of Alzheimer's disease and thus represents a new starting point for treating this disease. A subject of the invention is therefore the use of human PEM or a nucleic acid that codes for this as a target substance for the production of an agent for treating Alzheimer's disease. The inhibition of PEM can be carried out by a reduction of the expression of PEM. This can be carried out by antisense-nucleic acids, ribozymes or by substances that engage in the regulation mechanism of the PEM-gene expression. Such substances can be identified by a test system that measures the PEM-gene expression. Thus, e.g., cells that are trans-fixed with the PEM DNA can be brought into contact with the substances to be tested, and the expression of the PEM protein can be demonstrated, e.g., with the aid of antibodies.

In addition, PEM can also be inhibited on the protein level, e.g., by antibodies, peptides or low-molecular antagonists. Since PEM is a transcription factor, it is possible to inhibit the binding of PEM to DNA or the interaction with the transcription machinery.

The subject of the invention is also a process for the preparation of new agents for treating Alzheimer's disease. The identification of these new agents is carried out in that the ability of test substances to inhibit human PEM is determined. The function of the PEM as a transcription factor is measured. The binding of PEM to DNA can be measured. In contrast, cells can also be used that are transfected (transformed) with the gene for the human PEM. In these cells, the PEM protein is responsible for the gene regulation of other genes, so-called target genes. An inhibition of PEM by the test substances results in a reduction of the expression of the target genes.

Another subject of the invention is a cell that is transfected (transformed) with a DNA that codes for the human PEM or a fragment thereof and that contains at least one exogenous copy of this DNA. Still another subject of the invention is a cell that contains a defective PEM gene in at least one allele, for example a PEM gene that is disrupted by homologous recombination. These cells can be used just like the nucleic acids, which code for human PEM or a fragment thereof, or the human PEM protein itself or a fragment thereof for identifying and characterizing agents for birth control and for treatment of Alzheimer's disease.

Finally, the invention relates to a process for identifying genes that are regulated by the human PEM gene, whereby the influence of human PEM on the gene expression in human cells is tested. This test can be carried out, for example, by transcriptome analysis, e.g., according to the methods described by Kozian and Kirschbaum (Trends Biotechnol. 17 (1999), 73–78) or by proteome analysis according to the methods described by Dutt and Lee (Curr. Opin. Biotechnol. 11 (2000), 176–179). The genes that are identified by the process and their use as target substance for the production of an agent for birth control or for treatment of Alzheimer's disease are also subjects of this invention.

The invention is explained in more detail by the following FIGURE and example.

Figure 1:
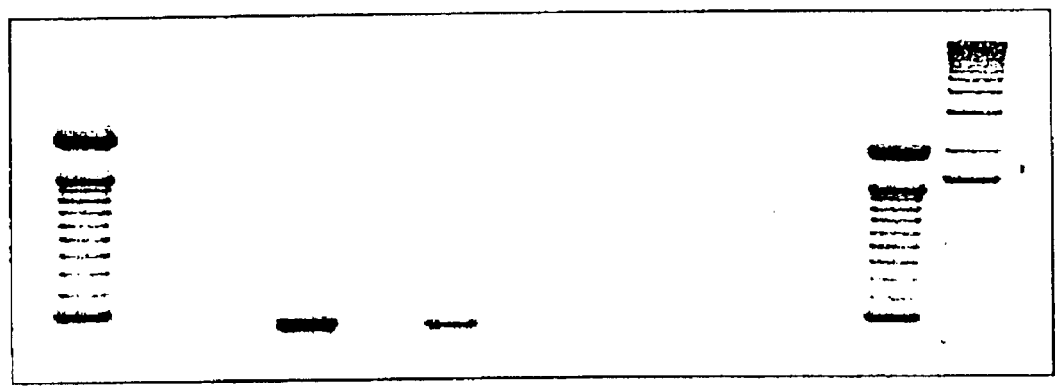
FIG. 1 shows the expression of human PEM mRNA in tissue samples from various parts of the brain.
Figure 1:
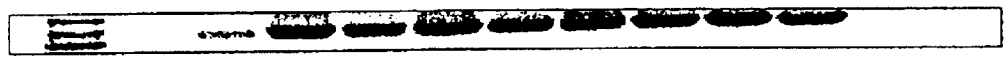

A. A sense primer as well as an antisense primer against the protein-coding section of the human PEM RNA were used for the PCR amplification. As a template, first-strand cDNA from various brain parts was used. The PCR products were separated on a 1.5% agarose gel and then stained with ethidium bromide. The human PEM amplificate can be detected at a size of about 550 bp. As size markers, the 1-kb markers and the 100-bp markers of Clontech were used. 1: 100-bp marker; 2: healthy brain, sample-a; 3: healthy temporal lobe; 4: temporal lobe with Alzheimer's disease; 5: healthy frontal lobe; 6: frontal lobe with Alzheimer's disease; 7: healthy hippocampus; 8: hippocampus tumor; 9: fetal brain; 10: healthy brain, sample-b; 11: water test; 12: 100-bp marker; 13: 1-kb marker.

B. A sense primer and an antisense primer against the protein-coding section of the beta-actin-RNA were used for the PCR amplification. As a template, the same first-strand cDNA as under A. was used. 1: 100-bp marker; 2: 1-kb marker; 3: healthy brain, sample-a; 4: healthy hippocampus; 5: hippocampus tumor; 6: healthy temporal lobe; 7: healthy frontal lobe; 8: temporal lobe with Alzheimer's disease; 9: frontal lobe with Alzheimer's disease; 10: fetal brain; 11: healthy brain, sample-b; 12: water test.

EXAMPLE

The expression of the human PEM in various brain tissues was analyzed by semi-quantitative PCR. To this end, the following primers were used:

Sense 5'-ATGGCGCGTTCGCTCGTCCACGAC-3' (SEQ ID NO: 5)

Antisense 5'-TAGTCCACGACGATGTAGACACAG-3' (SEQ ID NO: 5)

In the control, specific primers for beta-actin were used:

Sense primer 5'-CTAGAAGCATTTGCGGTGGACGATGGAGGG-3' (SEQ ID NO: 6)

Antisense primer 5'-CTAGAAGCATTTGCGGTGGACGATGGAGGG-3' (SEQ ID NO: 6)

The cDNA was acquired by Invitrogen (Carlsbad, Calif., USA). The PCR analysis was performed with the Advantage-2 PCR kit (Clontech). The reaction conditions were as follows: initially 5 minutes at 95° C.; then 30 cycles with 95° C. for 30 seconds, 62° C. for 30 seconds and 72° C. for 1 minute; finally 72° C. for 7 minutes. The results show an elevated expression of human PEM in the frontal and temporal lobes in Alzheimer patients in comparison to healthy tissue.

What is claimed is:

1. An isolated polynucleotide for a human PEM, comprising:
   (a) a polynucleotide sequence continuously coding for a polypeptide having the amino acid sequence set forth in SEQ ID NO:2;
   (b) a polynucleotide sequence as set forth in SEQ ID NO:1;
   (c) a polynucleotide sequence that hybridizes under stringent conditions to the polynucleotide sequence set forth in SEQ ID NO:1, and which continuously codes for a polypeptide, wherein said hybridization conditions comprises a wash for one hour in a solution comprising 1×SSC and 0.1% SDS at 62° C.; or
   complements thereto.

2. An isolated polynucleotide of claim 1, which comprises a polynucleotide sequence as set forth in SEQ ID NO:1, or a complement thereto.

3. An isolated polynucleotide of claim 1, which comprises a polynucleotide sequence continuously coding for a polypeptide having the amino acid sequence set forth in SEQ ID NO:2, or a complement thereto.

4. An isolated polynucleotide for a human PEM, comprising (a) a polynucleotide sequence continuously coding for a polypeptide having the amino acid sequence set forth in SEQ ID NO:2, which is specific for human PEM; (b) a polynucleotide sequence as set forth in SEQ ID NO:1 which is specific for human PEM; or complements thereto.

5. A transformed host cell that comprises at least one exogenous copy of a polynucleotide of claim 1.

6. A transformed host cell that comprises at least one exogenous copy of a polynucleotide of claim 4.

* * * * *